US009044498B2

(12) United States Patent
Coffey et al.

(10) Patent No.: US 9,044,498 B2
(45) Date of Patent: *Jun. 2, 2015

(54) LYOPHILIZED VIRAL FORMULATIONS

(75) Inventors: Matthew C. Coffey, Calgary (CA); Sarah Serl, Calgary (CA); Leo Pavliv, Cary, NC (US)

(73) Assignee: Oncolytics Biotech Inc., Calgary, Alberta (CA)

( * ) Notice: Subject to any disclaimer, the term of this patent is extended or adjusted under 35 U.S.C. 154(b) by 0 days.

This patent is subject to a terminal disclaimer.

(21) Appl. No.: 13/309,901

(22) Filed: Dec. 2, 2011

(65) Prior Publication Data

US 2012/0141528 A1 Jun. 7, 2012

Related U.S. Application Data

(60) Provisional application No. 61/419,020, filed on Dec. 2, 2010.

(51) Int. Cl.
| | |
|---|---|
| *A61K 35/76* | (2006.01) |
| *A61K 35/00* | (2006.01) |
| *A61P 35/00* | (2006.01) |
| *A61P 31/14* | (2006.01) |
| *A61P 37/04* | (2006.01) |
| *A61K 39/12* | (2006.01) |
| *A61K 39/15* | (2006.01) |
| *C12N 7/00* | (2006.01) |
| *A61K 9/00* | (2006.01) |
| *A61K 47/18* | (2006.01) |
| *A61K 47/02* | (2006.01) |
| *A61K 47/26* | (2006.01) |
| *A61K 9/19* | (2006.01) |

(52) U.S. Cl.
CPC ............... *A61K 35/765* (2013.01); *A61K 35/00* (2013.01); *C12N 2720/12251* (2013.01); *A61K 35/76* (2013.01); *A61K 35/768* (2013.01); *C12N 7/00* (2013.01); *A61K 9/0019* (2013.01); *A61K 47/183* (2013.01); *A61K 47/02* (2013.01); *A61K 47/26* (2013.01); *A61K 9/19* (2013.01)

(58) Field of Classification Search
None
See application file for complete search history.

(56) References Cited

U.S. PATENT DOCUMENTS

| | | | |
|---|---|---|---|
| 5,792,643 A | 8/1998 | Herrmann et al. | |
| 5,932,223 A * | 8/1999 | Burke et al. | 424/215.1 |
| 5,948,411 A | 9/1999 | Koyama et al. | |
| 6,051,238 A | 4/2000 | Volkin et al. | |
| 6,113,910 A | 9/2000 | Clark et al. | |
| 6,165,773 A | 12/2000 | New et al. | |
| 6,231,860 B1 | 5/2001 | Fanget et al. | |
| 6,258,362 B1 * | 7/2001 | Loudon et al. | 424/229.1 |
| 6,267,958 B1 | 7/2001 | Andya et al. | |
| 6,290,967 B1 | 9/2001 | Volkin et al. | |
| 6,290,991 B1 | 9/2001 | Roser et al. | |
| 6,403,098 B1 | 6/2002 | Burke et al. | |
| 6,451,256 B1 | 9/2002 | Sene | |
| 6,514,943 B2 | 2/2003 | Kovesdi et al. | |
| 6,518,239 B1 | 2/2003 | Kuo et al. | |
| 6,528,305 B2 | 3/2003 | Thompson et al. | |
| 6,541,001 B1 | 4/2003 | Gallili et al. | |
| 6,562,350 B1 * | 5/2003 | Wang et al. | 424/202.1 |
| 6,565,871 B2 | 5/2003 | Roser et al. | |
| 6,586,006 B2 | 7/2003 | Roser et al. | |
| 6,616,931 B1 | 9/2003 | Burke et al. | |
| 6,685,940 B2 | 2/2004 | Andya et al. | |
| 6,689,600 B1 * | 2/2004 | Wu et al. | 435/235.1 |
| 6,703,232 B2 | 3/2004 | Thompson et al. | |
| 6,808,916 B2 | 10/2004 | Coffey et al. | |
| 6,821,515 B1 | 11/2004 | Cleland et al. | |
| 6,893,657 B2 | 5/2005 | Roser et al. | |
| 7,049,127 B2 | 5/2006 | Thompson et al. | |
| 7,060,268 B2 | 6/2006 | Andya et al. | |
| 7,073,349 B2 | 7/2006 | Shekunov et al. | |
| 7,150,984 B2 | 12/2006 | Hoshino et al. | |
| 7,186,542 B2 | 3/2007 | Coffey et al. | |
| 7,223,585 B2 | 5/2007 | Coffey | |
| 7,351,415 B2 | 4/2008 | Evans et al. | |
| 7,456,009 B2 | 11/2008 | Evans et al. | |
| 7,803,385 B2 * | 9/2010 | Coffey | 424/215.1 |
| 7,901,921 B2 | 3/2011 | Coffey | |
| 8,313,897 B2 | 11/2012 | Drew | |
| 2001/0014326 A1 | 8/2001 | Andya et al. | |

(Continued)

FOREIGN PATENT DOCUMENTS

| | | |
|---|---|---|
| CN | 1765181 A | 5/2006 |
| EP | 1206189 | 6/2005 |

(Continued)

OTHER PUBLICATIONS

Grande A, Benavente J. Optimal conditions for the growth, purification and storage of the avian reovirus S1133. J Virol Methods. Mar. 2000;85(1-2):43-54.*

Arnold M, Patton JT, McDonald SM. Culturing, storage, and quantification of rotaviruses. Curr Protoc Microbiol. Nov. 2009;Chapter 15:Unit 15C.3.*

Wright JF, Le T, Prado J, Bahr-Davidson J, Smith PH, Zhen Z, Sommer JM, Pierce GF, Qu G. Identification of factors that contribute to recombinant AAV2 particle aggregation and methods to prevent its occurrence during vector purification and formulation. Mol Ther. Jul. 2005;12(1):171-8.*

(Continued)

*Primary Examiner* — Benjamin P Blumel
*Assistant Examiner* — Rachel Gill
(74) *Attorney, Agent, or Firm* — Kilpatrick, Townsend & Stockton LLP (57) ABSTRACT

Provided herein are lyophilized viral formulations useful for the stabilization and storage of viruses and methods of preparing these formulations. The lyophilized viral formulations described herein include a virus (e.g., a purified virus) and a non-viral composition including excipients. The formulations can be used, for example, to retain the infectivity or immunogenicity of viruses during periods of storage.

37 Claims, 4 Drawing Sheets

(56) References Cited

U.S. PATENT DOCUMENTS

| | | | |
|---|---|---|---|
| 2002/0041884 | A1 | 4/2002 | Evans et al. |
| 2002/0120228 | A1 | 8/2002 | Maa et al. |
| 2002/0168764 | A1 | 11/2002 | Coffey et al. |
| 2003/0059435 | A1 | 3/2003 | Gallili et al. |
| 2003/0153065 | A1 | 8/2003 | Kovesdi et al. |
| 2003/0180755 | A1 | 9/2003 | Hwang et al. |
| 2003/0186271 | A1 | 10/2003 | Hwang et al. |
| 2003/0202978 | A1 | 10/2003 | Maa et al. |
| 2004/0013695 | A1 | 1/2004 | Vande-Velde |
| 2004/0033239 | A1 | 2/2004 | Evans et al. |
| 2004/0042971 | A1 | 3/2004 | Truong-Le et al. |
| 2004/0042972 | A1 | 3/2004 | Truong-Le et al. |
| 2004/0092360 | A1 | 5/2004 | Semmes |
| 2004/0137013 | A1 | 7/2004 | Katinger et al. |
| 2005/0002969 | A1 | 1/2005 | Martyn |
| 2005/0032044 | A1 | 2/2005 | Setiwan |
| 2005/0147567 | A1 | 7/2005 | Kuo et al. |
| 2005/0175592 | A1 | 8/2005 | Wu et al. |
| 2005/0186225 | A1* | 8/2005 | Evans et al. ............... 424/233.1 |
| 2005/0226893 | A1 | 10/2005 | Juneau et al. |
| 2005/0266021 | A1 | 12/2005 | Maa et al. |
| 2006/0067943 | A1 | 3/2006 | Maa et al. |
| 2006/0088869 | A1 | 4/2006 | Coffey |
| 2006/0127415 | A1 | 6/2006 | Mayeresse |
| 2006/0165724 | A1 | 7/2006 | Thompson et al. |
| 2006/0257852 | A1 | 11/2006 | Rappuoli et al. |
| 2006/0263434 | A1 | 11/2006 | Desai et al. |
| 2006/0275306 | A1 | 12/2006 | Andya et al. |
| 2007/0148765 | A1 | 6/2007 | Evans et al. |
| 2007/0269856 | A1 | 11/2007 | Coffey |
| 2008/0166784 | A1* | 7/2008 | Chen et al. ............... 435/235.1 |
| 2008/0226602 | A1* | 9/2008 | Coffey ............... 424/93.2 |
| 2008/0241187 | A1 | 10/2008 | Calton et al. |
| 2008/0248551 | A1 | 10/2008 | Stinchcomb et al. |
| 2008/0261289 | A1 | 10/2008 | Frei et al. |
| 2008/0292594 | A1 | 11/2008 | Coffey et al. |
| 2008/0293123 | A1 | 11/2008 | Frei et al. |
| 2009/0047255 | A1 | 2/2009 | DePaz et al. |
| 2009/0098632 | A1 | 4/2009 | Frei et al. |
| 2009/0238797 | A1 | 9/2009 | Lang et al. |
| 2009/0258017 | A1 | 10/2009 | Callahan et al. |
| 2010/0028379 | A1 | 2/2010 | Tucker et al. |
| 2010/0226939 | A1* | 9/2010 | Truong-Le et al. ......... 424/215.1 |
| 2010/0233251 | A1 | 9/2010 | Von Andrian et al. |
| 2010/0247573 | A1 | 9/2010 | Vellom et al. |
| 2010/0260796 | A1* | 10/2010 | Belin-Poput et al. ...... 424/202.1 |
| 2012/0141421 | A1* | 6/2012 | Coffey et al. ............... 424/93.2 |
| 2012/0244158 | A1* | 9/2012 | Brige et al. ............... 424/135.1 |
| 2012/0273424 | A1* | 11/2012 | Coffey et al. ............... 210/656 |

FOREIGN PATENT DOCUMENTS

| | | |
|---|---|---|
| EP | 1526174 | 8/2007 |
| EP | 1137758 | 2/2008 |
| EP | 1133316 | 1/2009 |
| EP | 1501921 | 4/2009 |
| EP | 1135469 | 12/2009 |
| EP | 1741777 | 8/2010 |
| WO | 93/18790 | 9/1993 |
| WO | 95/10601 | 4/1995 |
| WO | 96/01651 | 1/1996 |
| WO | 97/04801 | 2/1997 |
| WO | 97/15331 | 5/1997 |
| WO | 98/02522 | 1/1998 |
| WO | 98/13065 | 4/1998 |
| WO | 98/28000 | 7/1998 |
| WO | 99/41416 | 8/1999 |
| WO | 99/62500 | 12/1999 |
| WO | 00/06196 | 2/2000 |
| WO | 00/61184 | 10/2000 |
| WO | 01/08495 | 2/2001 |
| WO | 01/13896 | 3/2001 |
| WO | 01/32144 | 5/2001 |
| WO | 01/66137 | 9/2001 |
| WO | 01/93829 | 12/2001 |
| WO | 02/11540 | 2/2002 |
| WO | 02/12435 | 2/2002 |
| WO | 03/043574 | 5/2003 |
| WO | 03/059292 | 7/2003 |
| WO | 03/061708 | 7/2003 |
| WO | 03/086443 | 10/2003 |
| WO | 03/087327 | 10/2003 |
| WO | 03/087339 | 10/2003 |
| WO | 2004/058156 | 7/2004 |
| WO | 2004/071410 | 8/2004 |
| WO | 2004/092360 | 10/2004 |
| WO | 2005/052116 | 6/2005 |
| WO | 2005/066333 | 7/2005 |
| WO | 2005/084646 | 9/2005 |
| WO | 2005/089712 | 9/2005 |
| WO | 2005/117962 | 12/2005 |
| WO | 2006/029467 | 3/2006 |
| WO | 2006/061708 | 6/2006 |
| WO | 2007/123961 | 11/2007 |
| WO | 2007/124090 | 11/2007 |
| WO | 2007/131972 | 11/2007 |
| WO | 2008006780 | 1/2008 |
| WO | 2008/039761 | 4/2008 |
| WO | 2008/058035 | 5/2008 |
| WO | 2008/106646 | 9/2008 |
| WO | 2009/014774 | 1/2009 |
| WO | 2009/042202 | 4/2009 |
| WO | 2009/056651 | 5/2009 |

OTHER PUBLICATIONS

Esfandiary R, Yee L, Ohtake S, Martin RA, Truong-Le VL, Lechuga-Ballesteros D, Moore DS, Joshi SB, Middaugh CR. Biophysical characterization of rotavirus serotypes G1, G3 and G4. Hum Vaccin. May 2010;6(5):390-8. Epub May 16, 2010.*

Figova K, Hrabeta J, Eckschlager T. Reovirus—possible therapy of cancer. Neoplasma. 2006;53(6):457-62.*

Chandran and Nibert, "Protease Cleavage of Reovirus Capsid Protein µ1/µ1C is Blocked by Alkyl Sulfate Detergents, Yielding a New Type of Infectious Subvirion Particle," Journal of Virology, 72(1):467-75 (1998).

Transfiguracion et al., "High yield purification of functional baculovirus vectors by size exclusion chromatography," Journal of Virological Methods, 142:21-28 (2007).

Transfiguracion et al., "Rapid and reliable quantification of reovirus type 3 by high performance liquid chromatography during manufacturing of Reolysin," Journal of Pharmaceutical and Biomedical Analysis, 48: 598-605 (2008).

International Search Report and Written Opinion issued in PCT/US2011/063037, mailed Jun. 26, 2012; 12 pages.

Huyghe et al., "Purification of a Type 5 Recombinant Adenovirus Encoding Human p53 by Column Chromatography," Human Gene Therapy, 6:1403-1416 (1995).

Kalbfuss et al., "Purification of Cell Culture-Derived Human Influenza A Virus by Size-Exclusion and Anion-Exchange Chromatography," Biotechnol Bioengin., 96(5): 932-944 (2007).

Peng et al., "A Rapid and Efficient Method for Purification of Recombinant Adenovirus with RGD-Modified Fibers," Anal. Biochem. 354(1): 140-147 (2006).

Australian Application No. 2011336410, First Examiner Report mailed on Jan. 6, 2014, 4 pages.

China Application No. 201180062149.7, First Office Action mailed Mar. 27, 2014, 15 pages.

Eurasian Application No. 201390812, Office Action mailed on Oct. 4, 2013, 2 pages.

European Application No. 11845053.5, Supplementary European Search Report mailed on Jan. 9, 2014, 1 page.

International Application No. PCT/US2011/063037, International Preliminary Report on Patentability mailed on Jun. 13, 2013, 8 pages.

Kang et al., "Development of a stabilizer for lyophilization of an attenuated duck viral hepatitis vaccine", Poultry Science Association, 89 (6): 1167-1170, 2010.

Tang et al., "Design of freeze-drying processes for pharmaceuticals: practical advice", Pharmaceutical Research, 21(2): 191-200, 2004.

(56) References Cited

OTHER PUBLICATIONS

Extended European Search Report issued in Application No. 11845053.5, mailed Dec. 10, 2013; 6 pages.
Chinese Application No. 201180062149.7, Third Office Action, Nov. 14, 2014, 7 pages, with English translation.
Song et al., Study on the preparation of the purified Japanese encephalitis vaccine with column chromatography, Progress in Microbiology and Immunology, 32(3), 9-11, Sep. 20, 2004. English language abstract.
CN Application No. 201180062149.7, Second Office Action, mailed Aug. 18, 2014, 9 pages.

* cited by examiner

LYOPHILIZED VIRAL FORMULATIONS

CROSS-REFERENCE TO PRIORITY APPLICATION

This application claims priority to U.S. Provisional Application No. 61/419,020, filed Dec. 2, 2010, which is incorporated herein by reference in its entirety.

BACKGROUND

Viruses are important in several therapeutic applications, including, for example, viral therapy and vaccine generation. In these therapeutic applications, it can be desirable for the viruses to retain their infectivity or immunogenicity. However, viruses often lose infectivity or immunogenicity after extended periods due to less than optimal formulations or unsuitable storage conditions.

SUMMARY

Provided herein are lyophilized viral formulations useful for the stabilization and storage of viruses and methods of preparing these formulations. The formulations can be used, for example, to preserve viruses (i.e., to retain the infectivity or immunogenicity of viruses) during periods of storage. The formulations can have lower levels of particulates, making them more suitable for parenteral infusion or injection.

The viral formulations described herein include a virus (e.g., a purified virus) and a non-viral composition including excipients. In some examples, the viral formulations include a purified virus and a non-viral composition comprising mannitol, sorbitol, histidine, and $Mg^{2+}$. In these examples, the viral formulations can be lyophilized. Prior to lyophilization, the non-viral composition is a liquid non-viral composition further comprising a liquid carrier. The concentration of sorbitol in the liquid non-viral composition can be less than 3% based on the weight of the liquid non-viral composition. The liquid non-viral composition, excluding the liquid carrier, can be substantially free of monovalent cationic salts.

In some examples, the viral formulations comprise a purified virus and a non-viral composition comprising mannitol, sorbitol, histidine, and $Mg^{2+}$. In these examples, the viral formulations can be lyophilized. Prior to lyophilization, the non-viral composition can be a liquid non-viral composition further comprising a liquid carrier. In some examples, the concentration of sugars in the liquid non-viral composition can be less than 7.5% by weight based on the weight of the non-viral composition.

The combined concentration of mannitol and sorbitol in the liquid non-viral composition can be less than 10% by weight (e.g., 7% by weight) based on the weight of the liquid non-viral composition. In some examples, the viral formulation is substantially free of $Zn^{2+}$ and/or trehalose. Optionally, the non-viral composition further includes a non-ionic surfactant.

The viral formulations described herein can comprise a purified virus and a non-viral composition comprising sucrose, $Mg^{2+}$, and a non-ionic surfactant. The viral formulations can be lyophilized. In these examples, the non-viral composition can be, prior to lyophilization, a liquid non-viral composition further comprising a liquid carrier. In these examples, the concentration of sucrose in the liquid non-viral composition, prior to lyophilization, is less than 5% based on the weight of the liquid non-viral composition. In these examples, the liquid non-viral compositions, excluding the liquid carrier, can be substantially free of monovalent cationic salts, non-sucrose polyols, and carboxylates.

Further, the viral formulations provided herein can consist essentially of a purified virus and a non-viral composition comprising sucrose, $Mg^{2+}$, and a non-ionic surfactant. In these examples, the viral formulations can be lyophilized. Prior to lyophilization, the non-viral composition can be a liquid non-viral composition further comprising a liquid carrier. The concentration of sucrose in the liquid non-viral composition can be less than 5% based on the weight of the liquid non-viral composition.

Optionally, $Mg^{2+}$ is present as magnesium chloride. The non-ionic surfactant is optionally polysorbate 80. The liquid carrier can be an aqueous carrier such as water. The virus included in the lyophilized viral formulations described herein can be, for example, an oncolytic virus and/or a non-enveloped virus. Provided herein is a lyophilized formulation in which the virus is a reovirus such as a mammalian reovirus. An example of a mammalian reovirus is a human reovirus, such as a serotype 3 virus (e.g., the Dearing strain reovirus). The reovirus is optionally a recombinant reovirus, a reassorted reovirus, or IDAC #190907-01.

Optionally, the viral formulations are stable at a temperature at about ambient temperature for a period of time (e.g., at least one day). Optionally, the viral formulations are stable at a temperature of about 4° C. or lower for at least three months (e.g., at least six months, at least twelve months, at least eighteen months, or any amount of time greater than three months). Optionally, the viral formulations are suitable for reconstitution before administration. Reconstituted viral formulations can be further diluted to achieve a preferred dose for administration.

Also provided herein are methods of making the viral formulations. The methods include providing the virus, combining the virus and a liquid non-viral composition (including the excipients as described herein and a liquid carrier) to form a liquid viral formulation, and lyophilizing the liquid viral formulation. Lyophilizing the liquid viral formulation optionally comprises the steps of freezing the liquid viral formulation to a temperature lower than 0° C. to form a frozen viral formulation and applying a vacuum to the frozen viral formulation. In some examples, the methods further comprise reconstituting the lyophilized viral formulation (e.g., dissolving or suspending the lyophilized viral formulation in a medium). The methods optionally further comprise adding a non-ionic surfactant to the composition. Viral formulations prepared according to these methods are also described herein.

Further described herein are methods of preserving or stabilizing a virus. The methods include preparing a lyophilized viral formulation as described herein and storing the lyophilized viral formulation. In some examples, the virus is stored at a temperature at or below ambient temperature. For example, the temperature can be ambient temperature or from 2° C. to 8° C. (e.g., 4° C.). In some examples, the temperature is −20° C. or from −60° C. to −80° C.

Additionally described herein are methods of preparing viral formulations with low levels of particulates prior to lyophilization, e.g., non-aggregating viral formulations. Optionally, the viral formulations comprise fewer than 6,000 particles having a particle size of 10 microns or greater per container (e.g., fewer than 3,000 particles, fewer than 2,000 particles, fewer than 1,000 particles, fewer than 500 particles, fewer than 300 particles, or fewer than 100 particles of 10 microns or greater per container). Optionally, the viral formulations comprise fewer than 600 particles having a particle size of 25 microns or greater (e.g., fewer than 500 particles, fewer than 400 particles, fewer than 300 particles, fewer than 200 particles, fewer than 100 particles, fewer than 50 particles, or fewer than 10 particles of 25 microns or greater per container). The methods include preparing the viral formulation as described herein and then lyophilizing the composition to prepare a lyophilized viral formulation. Optionally, the lyophilized viral formulation can be reconstituted and the reconstituted viral formulations can be suitable for administration by parenteral infusion or injection.

The details of one or more aspects are set forth in the accompanying drawings and the description below. Other features, objects, and advantages will be apparent from the description and drawings, and from the claims.

DETAILED DESCRIPTION

Described herein are viral formulations useful for the storage of viruses and methods of preparing these formulations. The formulations can be used, for example, to retain the infectivity or immunogenicity of viruses during periods of storage. The lyophilized viral formulations described herein include a virus and a non-viral composition including excipients.

Viruses for use in the lyophilized formulations described herein include enveloped and non-enveloped viruses. The enveloped and non-enveloped viruses can be DNA viruses, RNA viruses, or retroviruses. Optionally, the virus for use in the formulations described herein is a non-enveloped virus. Non-enveloped viruses include, for example, viruses belonging to the families of Adenoviridae (e.g., adenovirus), Picornaviridae (e.g., polio virus), Reoviridae (e.g., reovirus), Papillomaviridae (e.g., papilloma virus), Polyomaviridae (e.g., polyomavirus), Parvoviridae (e.g., Kilham rat virus), and Iridoviridae (e.g., tipula iridescent virus).

Optionally, the virus is an oncolytic virus. Suitable viruses for use in the formulations and methods described herein include, but are not limited to, myoviridae, siphoviridae, podoviridae, tectiviridae, corticoviridae, plasmaviridae, lipothrixviridae, fuselloviridae, poxyiridae, iridoviridae, phycodnaviridae, baculoviridae, herpesviridae, adenoviridae, papovaviridae, polydnaviridae, inoviridae, microviridae, geminiviridae, circoviridae, parvoviridae, hepadnaviridae, retroviridae, cystoviridae, reoviridae, birnaviridae, paramyxoviridae, rhabdoviridae, filoviridae, orthomyxoviridae, bunyaviridae, arenaviridae, leviviridae, picornaviridae, sequiviridae, comoviridae, potyviridae, caliciviridae, astroviridae, nodaviridae, tetraviridae, tombusviridae, coronaviridae, flaviviridae, togaviridae, barnaviridae, and bornaviridae viruses.

The lyophilized formulations optionally include a reovirus. As used herein, reovirus refers to any virus classified in the reovirus genus, including naturally occurring and recombinant reoviruses. Reoviruses are viruses with a double-stranded, segmented RNA genome. The virions measure 60-80 nm in diameter and possess two icosahedral, concentric capsid shells. The genome consists of double-stranded RNA in 10-12 discrete segments with a total genome size of 16-27 kilobase pairs (kbp). The individual RNA segments vary in size. Three distinct but related types of reovirus have been recovered from many species. All three types share a common complement-fixing antigen. The human reovirus consists of three serotypes: type 1 (strain Lang or T1L), type 2 (strain Jones, T2J), and type 3 (strain Dearing or strain Abney, T3D or T3A).

As described above, the reovirus can be a recombinant reovirus, which can be naturally occurring or non-naturally occurring. The reovirus is described as naturally occurring when it can be isolated from a source in nature and has not been intentionally modified by humans in the laboratory. For example, the reovirus can be from a field source (i.e., from a human who has been infected with the reovirus). The reovirus may also be selected or mutagenized for enhanced activity (e.g., oncolytic activity). Examples of specific reovirus can be found, for example, in U.S. Patent Application Publication Nos. 2008/0226602 and 2008/0292594.

The reovirus may be modified but still capable of lytically infecting a mammalian cell having an active ras pathway. The reovirus may be chemically or biochemically pretreated (e.g., by treatment with a protease, such as chymotrypsin or trypsin) prior to administration to the proliferating cells. Pretreatment with a protease removes the outer coat or capsid of the virus and may increase the infectivity of the virus. The reovirus may be coated in a liposome or micelle (Chandran and Nibert, *Journal of Virology*, 72(1):467-75 (1998)). For example, the virion may be treated with chymotrypsin in the presence of micelle-forming concentrations of alkyl sulfate surfactants to generate a new infectious subviral particle (ISVP).

The reovirus can be a recombinant or reassortant reovirus resulting from the recombination/reassortment of genomic segments from two or more genetically distinct reoviruses. Recombination/reassortment of reovirus genomic segments may occur in nature following infection of a host organism with at least two genetically distinct reoviruses. Recombinant virions can also be generated in cell culture, for example, by co-infection of permissive host cells with genetically distinct reoviruses. Accordingly, the recombinant reovirus for use in the formulations described herein can result from reassortment of genome segments from two or more genetically distinct reoviruses, including but not limited to, human reovirus, such as type 1 (e.g., strain Lang), type 2 (e.g., strain Jones), and type 3 (e.g., strain Dearing or strain Abney), non-human mammalian reoviruses, or avian reovirus. In some examples, the recombinant reoviruses can result from reassortment of genome segments from two or more genetically distinct reoviruses wherein at least one parental virus is genetically engineered, comprises one or more chemically synthesized genomic segments, has been treated with chemical or physical mutagens, or is itself the result of a recombination event. The recombinant reovirus can undergo recombination, for example, in the presence of chemical mutagens, including but not limited to dimethyl sulfate and ethidium bromide, or physical mutagens, including but not limited to ultraviolet light and other forms of radiation.

Other examples of suitable recombinant reoviruses include those that comprise deletions or duplications in one or more genome segments, that comprise additional genetic information as a result of recombination with a host cell genome, or that comprise synthetic genes. The reovirus can also be modified by incorporation of mutated coat proteins, such as for example al, into the virion outer capsid. The proteins can be mutated by replacement, insertion, or deletion. Replacement includes the insertion of different amino acids in place of the native amino acids. Insertions include the insertion of additional amino acid residues into the protein at one or more locations. Deletions include deletions of one or more amino acid residues in the protein. Such mutations can be generated by methods known in the art. For example, oligonucleotide site directed mutagenesis of the gene encoding for one of the coat proteins can result in the generation of the desired mutant coat protein. In one embodiment, the reovirus is IDAC #190907-01.

The viruses for use in the lyophilized formulations described herein can be purified viruses. As used herein, purified viruses refer to viruses that have been separated from cellular components that naturally accompany them. Typically, viruses are considered purified when they are at least 70% (e.g., at least 75%, at least 80%, at least 85%, at least 90%, at least 95%, or at least 99%) by dry weight, free from the proteins and other cellular components with which they are naturally associated. The viruses can be purified, for example, according to the methods described in U.S. Patent Application Publication Nos. 2002/0168764; 2004/0005693; 2005/0095692; 2006/0088869; and 2007/0269856, which are incorporated herein by reference in their entireties. For example, the virus can be separated from other particles using the techniques of density gradient centrifugation, ultrafiltration, diafiltration, ion exchange chromatography, size exclusion chromatography, high performance liquid chromatography, or combinations of these.

As discussed above, the viral formulations include a non-viral composition comprising excipients. Optionally, at least two excipients (e.g., two, three, or more excipients) are included in the non-viral composition. Excipients for use in the non-viral compositions include, but are not limited to, sugars, amino acids, divalent cations, and surfactants. These excipients can contribute to the stability of the virus. In some examples, the use of these excipients in the non-viral compositions and thus in the viral formulations allows for the long-term storage of viruses (e.g., storage for twelve months or greater) without loss of viral infectivity.

Suitable sugars for use in the non-viral compositions described herein include, for example, monosaccharides and disaccharides. In some examples, the non-viral compositions include mannitol, sorbitol, sucrose, or combinations of these. Further examples of suitable sugars include lactose, dextrose, fructose, glucose, and maltose. Optionally, the non-viral compositions and/or lyophilized viral formulations are substantially free of trehalose. Substantially free means that the non-viral compositions and/or lyophilized viral formulations can include less than 0.1%, less than 0.01%, less than 0.001%, less than 0.0001%, or 0% of trehalose based on the weight of the formulation. In some examples, the non-viral compositions and/or lyophilized viral formulations are substantially free of sugars other than sucrose (i.e., the non-viral compositions and/or lyophilized viral formulation is substantially free of non-sucrose polyols).

The sugars for use in the non-viral compositions and/or lyophilized viral formulations can include one sugar or a combination of two or more sugars. For example, the non-viral composition can include sucrose as the sugar present in the formulation or can include a combination of mannitol and sorbitol as the sugars present in the formulation. The concentration of excipients, including sugars, present in the lyophilized viral formulations can be expressed herein as the weight percent based on the weight of the liquid non-viral composition (i.e., the non-viral composition, prior to lyophilization, including a liquid carrier). The total concentration of sugar(s) present in the non-viral composition can be 10% by weight or less based on the weight of the non-viral composition. For example, the total concentration of sugars can be less than 7.5% by weight based on the weight of the liquid non-viral composition (e.g., less than 7.4% by weight, less than 7.3% by weight, less than 7.2% by weight, less than 7.1% by weight, less than 7% by weight, less than 6% by weight, less than 5% by weight, less than 4% by weight, less than 3% by weight, less than 2% by weight, or less than 1% by weight based on the weight of the liquid non-viral composition). For example, sucrose can be present in the non-viral composition in a concentration ranging from 0.1% to 5%, from 1% to 4.5%, or from 2% to 4% (e.g., 3%) by weight based on the weight of the liquid non-viral composition. Optionally, mannitol and sorbitol can be included in the non-viral composition in a combined concentration of less than 7.5% (e.g., 7%) based on the weight of the liquid non-viral composition. For instance, mannitol can be included in a concentration ranging from 0.01% to 7.4% (e.g., from 0.1% to 7%, from 1% to 6%, from 2% to 5%, or from 3% to 4%) and sorbitol can be included in a concentration ranging from 0.01% to 7.4% (e.g., from 0.1% to 7%, from 1% to 6%, from 2% to 5%, or from 3% to 4%), such that the combined concentration of the sugars is less than 7.5% based on the weight of the liquid non-viral composition.

Amino acids can also be included in the non-viral compositions described herein. Suitable amino acids include, for example, histidine, arginine, lysine, methionine, glutamic acid, or mixtures of these. One or more amino acids can be present in the non-viral composition in a concentration of 5% or less based on the weight of the liquid non-viral composition. For example, the concentration of amino acids can be 4.5% or less, 4.0% or less, 3.5% or less, 3.0% or less, 2.5% or less, 2.0% or less, 1.5% or less, 1.0% or less, or 0.5% or less based on the weight of the liquid non-viral composition.

Divalent cations can also be included in the non-viral compositions described herein. A suitable divalent cation for use in the non-viral composition includes the magnesium cation (i.e., $Mg^{2+}$). $Mg^{2+}$ can be introduced to the non-viral composition in combination with an anion as a salt, such as $MgCl_2$. Optionally, the non-viral compositions and/or viral formulations are substantially free of $Zn^{2+}$. The divalent cation can be present in the liquid non-viral composition in a concentration ranging from 0.01 mM to 5 mM. For example, $Mg^{2+}$ can be present in the viral formulation as $MgCl_2$ in a concentration ranging from 0.1 mM to 4.5 mM, 0.5 mM to 4 mM, or 1 mM to 3 mM (e.g., 2 mM). Optionally, the excipients present in the non-viral formulation, excluding the liquid carrier, can be substantially free of monovalent cationic salts, such as, for example, sodium ($Na^+$), lithium ($Li^+$), potassium ($K^+$), and ammonium ($NH_4^+$) containing salts.

A further excipient for use in the non-viral compositions described herein can include, for example, a surfactant. A surfactant refers to a substance having, in combination, a hydrophilic moiety and a hydrophobic moiety. As used herein, surfactants include, for example, detergents. Suitable surfactants for use in the non-viral compositions described herein include ionic and non-ionic surfactants. In some examples, polysorbate 80 is optionally included as the non-ionic surfactant in the non-viral compositions. One or more surfactants can be present in the non-viral compositions, optionally in an amount of less than 1% by weight based on the weight of the liquid non-viral composition. For example, the surfactant(s) can be present in the non-viral composition in an amount of less than 0.5% by weight, less than 0.1% by weight, or less than 0.05% by weight (e.g., 0.01% by weight).

Optionally, the non-viral compositions and/or lyophilized viral formulations are substantially free of carboxylates. Examples of carboxylates include succinate and citrate.

An exemplary combination of the virus and non-viral composition (including excipients) to form a viral formulation includes a purified virus, mannitol, sorbitol, histidine, and $Mg^{2+}$. As described above, the non-viral composition, prior to lyophilization, can further include (i.e., in addition to the excipients) a liquid carrier to form a liquid non-viral composition. The combined concentration of the sugars in the liquid non-viral composition can be less than 7.5% by weight based on the weight of the liquid non-viral composition. For example, the concentration of mannitol can be 3% and the concentration of histidine can be 2% to provide a combined concentration of 5%. Optionally, the sorbitol can be present in a concentration of less than 3% based on the weight of the liquid non-viral composition. For example, sorbitol can be present in a concentration of less than 2.9%, less than 2.8%, less than 2.7%, less than 2.6%, less than 2.5%, less than 2.4%, less than 2.3%, less than 2.2%, less than 2.1%, less than 2%, less than 1.9%, less than 1.8%, less than 1.7%, less than 1.6%, less than 1.5%, less than 1.4%, less than 1.3%, less than 1.2%, less than 1.1%, or less than 1%. The formulation can also include a non-ionic surfactant, such as polysorbate 80, in an amount less than 0.1% by weight of the liquid non-viral composition (e.g., 0.01%). Further, the non-viral composition and/or the viral formulation can be substantially free of monovalent cationic salts, $Zn^{2+}$, and/or trehalose.

Another suitable viral formulation includes a purified virus and a non-viral composition including sucrose, $Mg^{2+}$, and a non-ionic surfactant. Prior to lyophilization the non-viral composition can further include a liquid carrier, thus forming a liquid non-viral composition. The concentration of sucrose in the liquid non-viral composition can be less than 5% based on the weight of the liquid non-viral composition. Optionally, sucrose is present in a concentration of 4.5% or less, 4% or less, 3.5% or less, 3% or less, 2.5% or less, or 2% or less based on the weight of the liquid non-viral composition. Furthermore, the non-viral composition and/or the viral formulation can be substantially free of non-sucrose polyols and carboxylates (e.g., succinate and citrate).

Also described herein are methods of making the lyophilized viral formulations. The methods include providing a virus (e.g., a purified virus), combining the virus with a non-viral composition including the excipients in a liquid carrier to form a liquid viral formulation, and lyophilizing the liquid viral formulation. In some examples, a suitable amount of virus is provided to prepare a viral formulation at a titer ranging from $1\times10^5$ to $4\times10^{12}$ viral particles per milliliter (VP/mL) of liquid carrier.

Suitable liquid carriers can be aqueous or non-aqueous carriers. Examples of suitable non-aqueous carriers include propylene glycol, polyethylene glycol, and oils, including those of petroleum, animal, vegetable or synthetic origin, such as peanut oil, soybean oil, mineral oil, sesame oil, olive oil, and the like. Organic esters such as ethyl oleate are also suitable non-aqueous carriers. Aqueous carriers include water, ethanol, glycerol, alcoholic/aqueous solutions, emulsions, or suspensions, including saline and buffered media. Water or an aqueous carrier is preferred when the pharmaceutical composition is administered intravenously. Saline solutions and aqueous dextrose and glycerol solutions can also be employed as liquid carriers, particularly for injectable solutions. The composition, if desired, can also contain wetting or emulsifying agents, lubricants, glidants, emollients, humectants, thickeners, flavoring agents, preservatives, or pH buffers. pH buffers can be included to control the pH of the non-viral composition and thus, the viral formulation. In some examples, the buffer is included to maintain the pH of the viral formulation between 5 and 8.5. For example, the buffer can be included to maintain the pH of the viral formulation between 6.8 and 8.0 or between 7.0 and 7.8 (e.g., 7.4). Examples of suitable buffers include phosphate buffers such as phosphate buffered saline (PBS), e.g., 0.01-0.1 M and preferably 0.05 M phosphate buffer, acetate buffers, benzoate buffers, citrate buffers, lactate buffers, maleate buffers, and tartrate buffers. Buffered carriers like Hanks's solution, Ringer's solution, dextrose solution, 5% human serum albumin, Ringer's dextrose, dextrose and sodium chloride, lactated Ringer's and fixed oils, polyethylene glycol, polyvinyl pyrrolidone, or lecithin can be used. Monoethanolamine, diethanolamine, tromethamine, and glycine solutions can also be used as suitable buffers. Liposomes and nonaqueous vehicles such as fixed oils may also be used as carriers. Further examples of suitable carriers are described in "Remington's Pharmaceutical Sciences" by E. W. Martin. The formulation should suit the mode of administration.

Alternatively, the non-viral composition containing the excipients in a liquid carrier can be added to a culture of cells infected with virus. As used herein, a culture of cells refers to a population of cultured cells as found in their culture conditions (e.g., the cells infected with virus and the culture medium).

Lyophilization can be performed using techniques and equipment as known in the art. The lyophilization process can be performed, for example, using a lyophilizer. Lyophilizing can involve freezing and subsequently drying the liquid viral formation. Optionally the lyophilization involves a product loading stage, freezing stage and primary drying and secondary drying stage. The product is loaded into the lyophilizer and the shelves are set to a target temperature setpoint for a pre-determined duration. The freezing stage involved the shelves being chilled to a target set point at a controlled rate (° C./hr). The product is maintained at the freezing stage for a pre-determined amount of time. In the freezing step, the liquid viral formulation can be cooled, for an appropriate period of time, to a temperature lower than 0° C. to form a frozen viral formulation. Optionally, the liquid viral formulation can be cooled to a temperature of −50° C. or lower. In some examples, the liquid viral formulation can be cooled for 10 hours or less. For example, the viral formulation can be cooled for 9 hours or less, 8 hours or less, 7 hours or less, 6 hours or less, 5 hours or less, 4 hours or less, 3 hours or less, 2 hours or less, 1 hour or less, or 30 minutes or less. Optionally, the lyophilization process can include an annealing step wherein the frozen viral formulation is warmed to a temperature at or below ambient temperature, and then cooled again to form a frozen viral formulation. In some examples, the annealing step is not performed. The frozen viral formulation can then be dried under reduced pressure (e.g., by applying a vacuum) to form the lyophilized viral formulation. Optionally, a vacuum pressure ranging from 50 to 80 µm Hg (e.g., 60 µm Hg) can be applied to the frozen viral formulation. The drying step can be performed at a temperature at, below, or above ambient temperature. For example, the drying step can be performed at a temperature of 40° C. or less, 30° C. or less, 20° C. or less, 10° C. or less, or 0° C. or less. Optionally, the lyophilized viral formulation can be further dried in one or more additional drying steps at a temperature at, below, or above ambient temperature to remove residual water. For example, the additional drying steps can be performed at a temperature ranging from −10° C. to 50° C. (e.g., from 0° C. to 40° C., from 10° C. to 30° C., or from 20° C. to 25° C.). Furthermore, the lyophilized viral formulation can be dried in the presence of an inert gas (e.g., nitrogen) or a combination of inert gasses. For example, the lyophilization vessel and/or the viral storage container can be purged with an inert gas and capped to avoid exposure of the viral formation to the air. The lyophilized viral formulation, after one or more drying steps, can have a moisture content of, for example, less than 20%. In some examples, the moisture content of the lyophilized viral formulation is less than 15%, less than 10%, less than 5%, less than 4%, less than 3%, less than 2%, less than 1%, less than 0.5%, or less than 0.1%.

The lyophilized viral formulations described herein can be used to preserve and stabilize a virus for a period of time, including extended storage periods. For example, the virus prepared according to the formulations described herein can be stored for up to twelve months (e.g., one day, one week, one month, three months, six months, nine months, or twelve months) without losing viral infectivity. The lyophilized viral formulations described herein are stable at about ambient temperature and may exhibit increased stability at temperatures lower than about ambient temperature. As used herein, ambient temperature refers to a temperature between about 10° C. and about 30° C. Viruses can be stored in the viral formulations at temperatures below ambient temperature without significant loss of infectivity or immunogenicity. In some examples, the lyophilized viral formulations are stored at temperatures of 9° C. and lower (e.g., 8° C. and lower, 7° C. and lower, 6° C. and lower, 5° C. and lower, 4° C. and lower, 3° C. and lower, 2° C. and lower, and 1° C. and lower. For example, the storage temperature can range from 2° C. to 8° C. (e.g., 4° C.). Further, the lyophilized viral formulations can be stored at temperatures below 0° C., such as, for example, −20° C. or from −60° C. to −80° C., while maintaining viral infectivity.

The lyophilized viral formulations are stable, for example, at a temperature at about ambient temperature for a period of time (e.g., at least one day). In some examples, the viral formulations are stable at a temperature of about 4° C. or lower for at least three months (e.g., at least four months, at least five months, at least six months, at least seven months, at least eight months, at least nine months, at least ten months, at least eleven months, at least twelve months, at least thirteen months, at least fourteen months, at least fifteen months, at least sixteen months, at least seventeen months, at least eighteen months, or any amount of time greater than three months). Additionally described herein are methods of preparing viral formulations with low levels of particulates, e.g., low or non-aggregating viral formulations. The methods include preparing the viral formulation as described herein and then lyophilizing the formulation to prepare a lyophilized viral formulation. The viral formulations prepared according to these methods include low levels of particulates and are thus suitable for administration by parenteral infusion or injection. In some examples, the levels of particulates in the methods are determined using the light obscuration particle count test and/or the microscopic particle count test according to USP <788>, which is incorporated herein in its entirety. Optionally, the viral formulations comprise fewer than 6,000 particles having a particle size of 10 microns or greater per container. For example, the viral formulations can comprise fewer than 5,000 particles, fewer than 4,000 particles, fewer than 3,000 particles, fewer than 2,000 particles, fewer than 1,000 particles, fewer than 900 particles, fewer than 800 particles, fewer than 700 particles, fewer than 600 particles, fewer than 500 particles, fewer than 400 particles, fewer than 300 particles, fewer than 200 particles, or fewer than 100 particles of 10 microns or greater per container. Optionally, the viral formulations comprise fewer than 600 particles having a particle size of 25 microns or greater (e.g., fewer than 500 particles, fewer than 400 particles, fewer than 300 particles, fewer than 200 particles, fewer than 100 particles, fewer than 50 particles, or fewer than 10 particles of 25 microns or greater per container).

Further provided herein are pharmaceutical compositions including the lyophilized viral formulations. The herein provided compositions can be administered in vitro or in vivo in a pharmaceutically acceptable carrier. Optionally, the lyophilized viral formulations can be reconstituted by dissolving or suspending the lyophilized viral formulation in a medium prior to combining with a pharmaceutically acceptable carrier. A pharmaceutically acceptable carrier can be a solid, semi-solid, or liquid material that can act as a vehicle, carrier, or medium for the lyophilized viral formulation. Thus, the lyophilized viral formulation can be in the form of tablets, soft or hard gelatin capsules, suspensions, emulsions, solutions, syrups, aerosols (in a liquid medium), and sterile injectable solutions. Optionally, the lyophilized viral formulations are suitable for infusion. In these examples, the lyophilized viral formulations prepared according to the methods described herein can be reconstituted and further diluted, as appropriate, for infusion. For example, the non-aggregating viral formulations having lower levels of particulates as described herein can be reconstituted and the reconstituted viral formulations can be suitable for parenteral infusion or injection.

A pharmaceutical composition additionally can include, without limitation, lubricating agents such as talc, magnesium stearate, and mineral oil; wetting agents; emulsifying and suspending agents; preserving agents such as methyl- and propylhydroxy-benzoates; sweetening agents; and flavoring agents. Pharmaceutical compositions can be formulated to provide quick, sustained, or delayed release of the virus included in the lyophilized viral formulation after administration by employing procedures known in the art. In addition to the representative formulations described below, other suitable formulations for use in a pharmaceutical composition can be found in Remington: The Science and Practice of Pharmacy (21th ed.) ed. David B. Troy, Lippincott Williams & Wilkins, 2005.

Liquid formulations that include the lyophilized viral formulations (e.g., reconstituted lyophilized viral formulations) for oral administration or for injection generally include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Another formulation that is optionally employed in the methods of the present disclosure includes transdermal delivery devices (e.g., patches). Such transdermal delivery can be used to provide continuous or discontinuous infusion of the virus included in the lyophilized viral formulations as described herein. The construction and use of transdermal patches for the delivery of pharmaceutical agents is well known in the art. See, for example, U.S. Pat. No. 5,023,252. Such patches can be constructed for continuous, pulsatile, or on-demand delivery of the viruses.

In the provided methods, the lyophilized viral formulation is administered in a manner so that the virus can ultimately contact the target cells, for example, systemically. The route by which the viral formulation is administered depends on the location as well as the type of the target cells. A wide variety of administration routes can be employed. For vaccines, the virus can be administered systemically, intradermally, or subcutaneously, so as to target antigen presenting cells, so as to elicit an immune response. For oncolytic viruses where the target is an accessible solid tumor, the viral formulation can be administered by injection directly to the tumor or intravenously. Optionally, the formulation is suitable for reconstitution prior to administration. For a hematopoietic tumor, for example, the viral formulation can be reconstituted and administered intravenously or intravascularly. For tumors that are not easily accessible within the body, such as metastases, the viral formulation can be administered in a manner such that it can be transported systemically through the body of the mammal and thereby reach the tumor (e.g., intravenously or intramuscularly). Alternatively, the viral formulation can be administered directly to a single solid tumor, where it then is carried systemically through the body to metastases. For vaccine or oncolytic therapy, the viral formulation can also be administered subcutaneously, intraperitoneally, intrathecally (e.g., for brain tumor), topically (e.g., for melanoma), orally (e.g., for oral or esophageal cancer), rectally (e.g., for colorectal cancer), vaginally (e.g., for cervical or vaginal cancer), nasally, by inhalation spray or by aerosol formulation (e.g., for lung cancer).

Optionally, the viral formulation is administered continuously to a subject at least once per day or up to throughout the day on consecutive days, for a period of time. For vaccine administration, typically a prime and one or more boost administrations are necessary. Thus, the viral formulation is administered, for example, to a subject in any pharmacologically acceptable solution (e.g., by intravenous administration or infusion) over a period of time or intermittently. For example, the formulation may be administered systemically by injection (e.g., IM or subcutaneously) or taken orally daily at least once per day, or administered by infusion in a manner that results in the daily delivery into the tissue or blood stream of the subject. When the viral formulation is administered by infusion over a period of time, the period of time is, for example, 1, 2, 3, 4, 5, 6, 7, 8, 9, 10, 12, or 24 hours, or any time between 1 and 24 hours, inclusive, or more. Optionally, the period of time is 5, 15, 30, 60, 90, 120, 150 or 180 minutes, or any time between 5 and 180 minutes, inclusive, or more. Thus, for example, the viral formulation is administered by infusion for 60 minutes. Administrations can be repeated daily for 2, 3, 4, 5, 6, 7, 8, 9, 10, 14, 21, 28 days, or any number of days between 2 and 28 days, inclusive, or longer.

Optionally, the viral formulation includes an adjuvant when used to elicit an immune response. Adjuvants include, for example, aluminum salts, mineral oil, particulates, lipopolysaccharides, saponins, and the like.

The viral formulations as disclosed herein can be administered in an amount that is sufficient (i.e., an effective amount) to treat a proliferative disorder or to elicit an immune response. A proliferative disorder is treated when administration of the liquid virus formulation to proliferating cells affects lysis (e.g., oncolysis) of the affected cells, resulting in a reduction in the number of abnormally, proliferating cells, a reduction in the size of a neoplasm, and/or a reduction in or elimination of symptoms (e.g., pain) associated with the proliferating disorder. As used herein, the term oncolysis means at least 10% of the proliferating cells are lysed (e.g., at least about 20%, 30%, 40%, 50%, or 75% of the cells are lysed). The percentage of lysis can be determined, for example, by measuring the reduction in the size of a neoplasm or in the number of proliferating cells in a mammal, or by measuring the amount of lysis of cells in vitro (e.g., from a biopsy of the proliferating cells).

An effective amount of the viral formulation will be determined on an individual basis and may be based, at least in part, on the particular virus used in the viral formulation; the individual's size, age, gender; the goal of the treatment (e.g., to treat a proliferative disease or to elicit an immune response); and the size and other characteristics of the abnormally proliferating target cells. The viral concentration in the viral formulation can be measured by determining the number of plaque forming units (PFU) in plaque based assays. For example, for treatment of a human with a proliferative disease, approximately $10^3$ to $10^{12}$ PFU of a virus contained in a viral formulation are used, depending on the type, size, and number of proliferating cells or neoplasms present. The effective amount can be, for example, from about 1.0 PFU/kg body weight to about $10^{15}$ PFU/kg body weight (e.g., from about $10^2$ PFU/kg body weight to about $10^{13}$ PFU/kg body weight). For example, the effective amount of the viral formulation administered daily can be $1\times10^{10}$ PFU and the viral formulation can be administered over five days to result in a total treatment amount of $5\times10^{10}$. Optionally, the viral concentration in the viral formulation can be measured by determining the 50% tissue culture infective dose ($TCID_{50}$), which is the amount of virus required to produce a cytopathic effect in 50% of cells infected with the virus. In some examples, the ratio between $TCID_{50}$ and PFU is 3:1. The effective amount of the viral formulation for treating a human with a proliferative disease can be from about $1\times10^8$ to about $1\times10^{15}$ TCID$_{50}$ per day. The effective amount of the viral formulation can be administered over a period of time, referred to herein as a cycle. A cycle can represent, for example, one day, two days, three days, four days, five days, six days, seven days, eight days, nine days, or ten days, where an equal or different amount of the viral formulation can be administered daily. For example, $3\times10^{10}$ TCID$_{50}$ per day can be administered over five days to result in a total amount of $1.5\times10^{11}$ TCID$_{50}$ per cycle. Optionally, the effective amount is about $3\times10^{10}$ TCID$_{50}$ per day. Optionally, the viral formulation is administered as a one hour intravenous infusion.

Optimal dosages of the viral formulations depend on a variety of factors. The exact amount required will vary from subject to subject, depending on the species, age, weight and general condition of the subject, the severity of the disease being treated, the particular virus used in the formulation, and its mode of administration. Thus, it is not possible to specify an exact amount for every formulation. However, an appropriate amount can be determined by one of ordinary skill in the art using only routine experimentation given the guidance provided herein.

The dosage ranges for the administration of the formulations are those large enough to produce the desired effect in which the symptoms of the disease are affected or large enough to elicit an immune response. The dosage should not be so large as to cause adverse side effects, such as unwanted cross-reactions and anaphylactic reactions. The dosage can be adjusted by the individual physician in the event of any contraindications.

Dosages vary and are administered in one or more dose administrations daily, for one or several days. The provided viral formulation can be administered in a single dose or in multiple doses (e.g., two, three, four, six, or more doses). For example, where the administration is by infusion, the infusion can be a single sustained dose or can be delivered by multiple infusions. Treatment may last from several days to several months or until diminution of the disease is achieved.

Combinations of the viral formulations can be administered either concomitantly (e.g., as an admixture), separately but simultaneously (e.g., via separate intravenous lines into the same subject), or sequentially (e.g., one of the formulations is given first followed by the second). Thus, the term combination is used to refer to either concomitant, simultaneous, or sequential administration of two or more agents.

It is contemplated that the provided viral formulations may be combined with other tumor therapies such as chemotherapy, radiotherapy, surgery, hormone therapy, and/or immunotherapy. Thus, the viral formulations may be administered in conjunction with surgery or removal of the neoplasm. Therefore, provided herewith are methods for the treatment of a solid neoplasm comprising surgical removal of the neoplasm and administration of the viral formulation at or near to the site of the neoplasm.

It is further contemplated that the viral formulations in the provided methods are, optionally, administered in combination with or in addition to known anticancer compounds or chemotherapeutic agents. Chemotherapeutic agents are compounds which may inhibit the growth of tumors. Such agents, include, but are not limited to, antineoplastic agents such as Acivicin; Aclarubicin; Acodazole Hydrochloride; AcrQnine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflomithine Hydrochloride; Elsamitrucin; Enloplatin; Enpromate; Epipropidine; Epirubicin; Epirubicin Hydrochloride; Erbulozole; Esorubicin Hydrochloride; Estramustine; Estramustine Phosphate Sodium; Etanidazole; Ethiodized Oil I 131; Etoposide; Etoposide Phosphate; Etoprine; Fadrozole Hydrochloride; Fazarabine; Fenretinide; Floxuridine; Fludarabine Phosphate; 5-Fluorouracil; Fluorocitabine; Fosquidone; Fostriecin Sodium; Gemcitabine; Gemcitabine Hydrochloride; Gold Au 198; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-I a; Interferon Gamma-I b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin C; Mitosper; Mitotane; Mitoxantrone; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride.

Further examples of anti-neoplastic compounds include 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; atrsacrine; anagrelide; anastrozole; andrographolide; angiogenesis inhibitors; antagonist D; antagonist G; antarelix; anthracyclines; anti-dorsalizing morphogenetic protein-1; antiandrogens, prostatic carcinoma; antiestrogens; antineoplastons; antisense oligonucleotides; aphidicolin glycinate; apoptosis gene modulators; apoptosis regulators; apurinic acid; ara-CDP-DL-PTBA; arginine deaminase; aromatase inhibitors; asulacrine; atamestane; atrimustine; axinastatin 1; axinastatin 2; axinastatin 3; azasetron; azatoxin; azatyrosine;

baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docosanol; dolasetron; doxifluridine; droloxifene; dronabinol; duocannycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; fmasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hormone therapies; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; irinotecan; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; LHRH analogs; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance genie inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; progestational agents; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfmosine; superactive vasoactive intestinal peptide antagonist; suradista; suramin; swainsonine; synthetic glycosaminoglycans; tallimustine; tamoxifen; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thalidomide; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene dichloride; topotecan; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer.

Further examples of chemotherapeutic agents suitable for use in the viral formulations described herein include anticancer supplementary potentiating agents, including tricyclic anti-depressant drugs (e.g., imipramine, desipramine, amitryptyline, clomiprainine, trimipramine, doxepin, nortriptyline, protriptyline, amoxapine and maprotiline); non-tricyclic anti-depressant drugs (e.g., sertraline, trazodone and citalopram); agents that recognize or block VEGF (e.g., Avastin); $Ca^{2+}$ antagonists (e.g., verapamil, nifedipine, nitrendipine and caroverine); Calmodulin inhibitors (e.g., prenylamine, trifluoroperazine and clomipramine); Amphotericin B; Triparanol analogues (e.g., tamoxifen); antiarrhythmic drugs (e.g., quinidine); antihypertensive drugs (e.g., reserpine); antibodies to receptors, such as herceptin; thiol depleters (e.g., buthionine and sulfoximine); and multiple drug resistance reducing agents such as Cremaphor EL. The viral formulations described herein can also be administered with cytokines such as granulocyte colony stimulating factor.

As used herein, the term proliferative disorder refers to any cellular disorder in which the cells proliferate more rapidly than normal tissue growth. A proliferative disorder includes, but is not limited to, neoplasms, which are also referred to as tumors. A neoplasm can include, but is not limited to, pancreatic cancer, breast cancer, brain cancer (e.g., glioblastoma), lung cancer, prostate cancer, colorectal cancer, thyroid cancer, renal cancer, adrenal cancer, liver cancer, neurofibromatosis 1, and leukemia. A neoplasm can be a solid neoplasm (e.g., sarcoma or carcinoma) or a cancerous growth affecting the hematopoietic system (e.g., lymphoma or leukemia). Other proliferative disorders include, but are not limited to neurofibromatosis.

As used herein the terms treatment, treat, treating or ameliorating refers to a method of reducing the effects of a disease or condition or symptom of the disease or condition. Thus in the disclosed method, treatment can refer to a 10%, 20%, 30%, 40%, 50%, 60%, 70%, 80%, 90%, or 100% reduction or amelioration in the severity of an established disease or condition or symptom of the disease or condition. For example, the method for treating cancer is considered to be a treatment if there is a 10% reduction in one or more symptoms of the disease in a subject as compared to control. Thus the reduction can be a 10, 20, 30, 40, 50, 60, 70, 80, 90, 100%, or any percent reduction in between 10 and 100 as compared to native or control levels. It is understood that treatment does not necessarily refer to a cure or complete ablation of the disease, condition, or symptoms of the disease or condition.

As used herein, the term subject can be a vertebrate, more specifically a mammal (e.g., a human, horse, pig, rabbit, dog, sheep, goat, non-human primate, cow, cat, guinea pig or rodent), a fish, a bird or a reptile or an amphibian. The term does not denote a particular age or sex. Thus, adult and newborn subjects, whether male or female, are intended to be covered. As used herein, patient or subject may be used interchangeably and can refer to a subject with a disease or disorder. The term patient or subject includes human and veterinary subjects.

Throughout this application, various publications are referenced. The disclosures of these publications in their entireties are hereby incorporated by reference into this application.

A number of aspects have been described. Nevertheless, it will be understood that various modifications may be made. Furthermore, when one characteristic or step is described it can be combined with any other characteristic or step herein even if the combination is not explicitly stated. Accordingly, other aspects are within the scope of the claims.

EXAMPLES

Example 1

Non-Viral Composition Preparation

Compositions 1 and 2 were prepared by mixing the components shown in Table 1.

TABLE 1

|  | Composition 1 | | Composition 2 | |
| --- | --- | --- | --- | --- |
|  | Component | Amount | Component | Amount |
| Sugar(s) | Mannitol | 30 mg/mL | Sucrose | 40 mg/mL |
|  | Sorbitol | 20 mg/mL |  |  |
| Amino Acid | Histidine | 20 mg/mL | N/A | N/A |
| Divalent Cation | MgCl$_2$ (2 mM) | 2 mM | MgCl$_2$ | 2 mM |
| Surfactant | Polysorbate 80 | 0.01% | Polysorbate 80 | 0.05% |
| Carrier | Phosphate Buffered Saline (PBS) |  | Phosphate Buffered Saline (PBS) |  |

The PBS used contained 0.20 mg/mL potassium chloride, 8.00 mg/mL sodium chloride, 0.24 mg/mL monobasic potassium phosphate, and 2.71 mg/mL dibasic sodium phosphate heptahydrate.

Example 2

Lyophilized Viral Formulation Preparation

A control reovirus formulation (Control Formulation) was prepared by providing reovirus in phosphate buffered saline (PBS), further diluting the mixture with additional PBS to obtain a target total viral particle titer of $3\times10^{10}$ TCID$_{50}$/mL, and lyophilizing the viral formulation. Formulation 1 was prepared by providing reovirus in PBS, diluting the mixture with Composition 1 to obtain a target total viral particle titer of $3\times10^{10}$ TCID$_{50}$/mL, and lyophilizing the viral formulation. Formulation 2 was prepared by providing reovirus in PBS, diluting the mixture with Composition 2 to obtain a target total viral particle titer of $3\times10^{10}$ TCID$_{50}$/mL, and lyophilizing the viral formulation.

To lyophilize the viral formulations, each diluted composition was individually added to a lyophilization vessel and placed on a shelf within an ADVANTAGE PLUS EL-85 BENCHTOP FREEZE DRYER (The Virtis Co., Inc; Gardiner, N.Y.). The shelves were set to a target temperature setpoint of 5° C. and compositions were maintained at this temperature for 120 minutes. The compositions were then cooled, at a rate of 15° C. per hour, to −50° C. and the composition was maintained at −50° C. for three hours. The condenser of the lyophilizer was then cooled to a temperature between −75° C. and −50° C. and the chamber was evacuated to a target pressure of 60 μm Hg. The chamber pressure was controlled by adding 0.2 μm of filtered ambient air into the chamber. The compositions were then warmed to −35° C. over 30 minutes and were dried at this temperature for 48 hours. The temperature was then raised to 25° C. and the compositions were dried for an additional 15 hours at this temperature. The dilution ratios for each of the formulations were determined by analytical HPLC.

Example 3

Lyophilized Viral Formulation Storage

Figure 1:
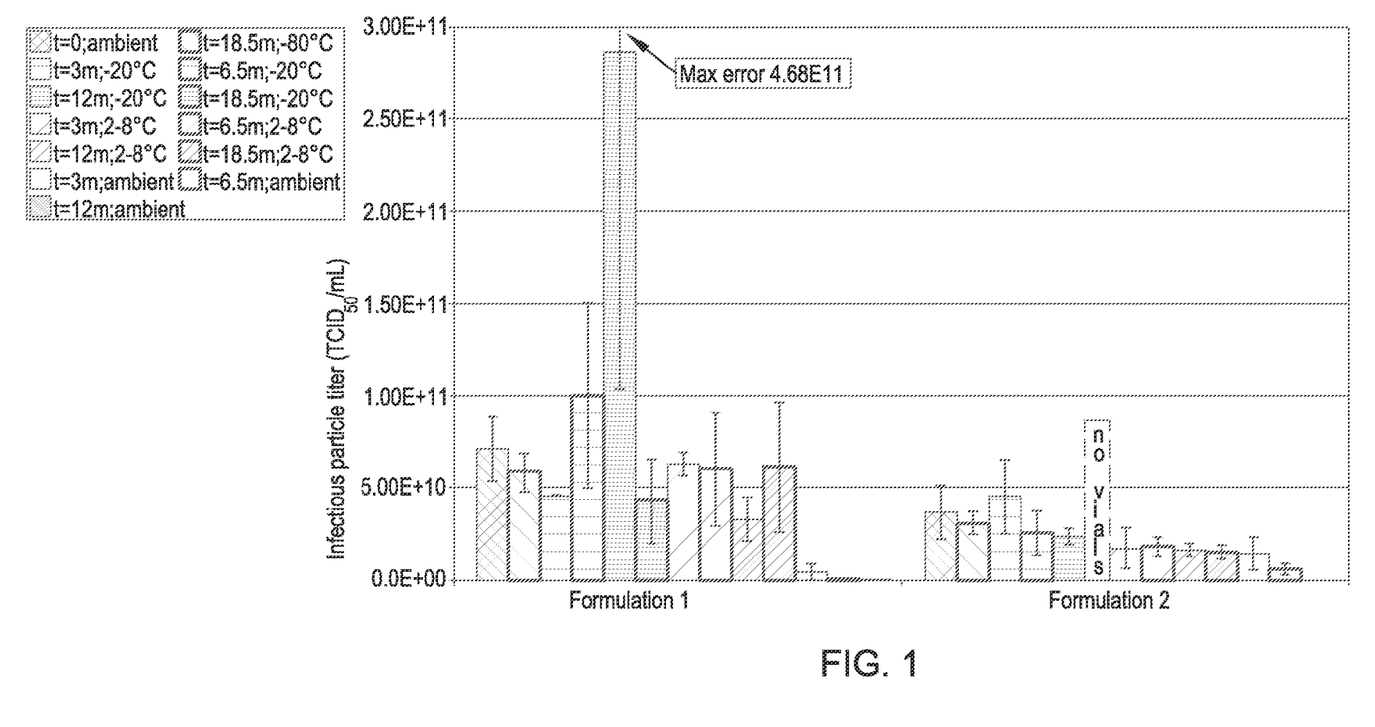
FIG. 1 is a bar graph showing the median tissue culture infective dose, expressed as $TCID_{50}$ per milliliter, for lyophilized reovirus formulations prior to storage (t=0) at ambient temperature and after 3 (t=3 m), 6.5 (t=6.5 m), 12 (t=12 m), and 18.5 (t=18.5 m) months of storage at ambient temperature, 2-8° C., −20° C., and −80° C. For each formulation, from left to right: t=0 at ambient temperature; t=18.5 m at −80° C.; t=3 m at −20° C.; t=6.5 m at −20° C.; t=12 m at −20° C.; t=18.5 m at −20° C.; t=3 m at 2-8° C.; t=6.5 m at 2-8° C.; t=12 m at 2-8° C.; t=18.5 m at 2-8° C.; t=3 m at ambient temperature; t=6.5 m at ambient temperature; t=12 m at ambient temperature. For Formulation 1, phosphate buffered saline-eluted reovirus was diluted in 30 mg/mL mannitol, 20 mg/mL histidine, 0.01% v/v polysorbate 80, 20 mg/mL sorbitol, and 2 mM $MgCl_2$, to a viral titer of $3 \times 10^{10}$ $TCID_{50}$/mL. For Formulation 2, phosphate buffered saline-eluted reovirus was diluted in 40 mg/mL sucrose, 0.05% v/v polysorbate 80, and 2 mM $MgCl_2$, to a viral titer of $3 \times 10^{10}$ $TCID_{50}$/mL.
Figure 2:
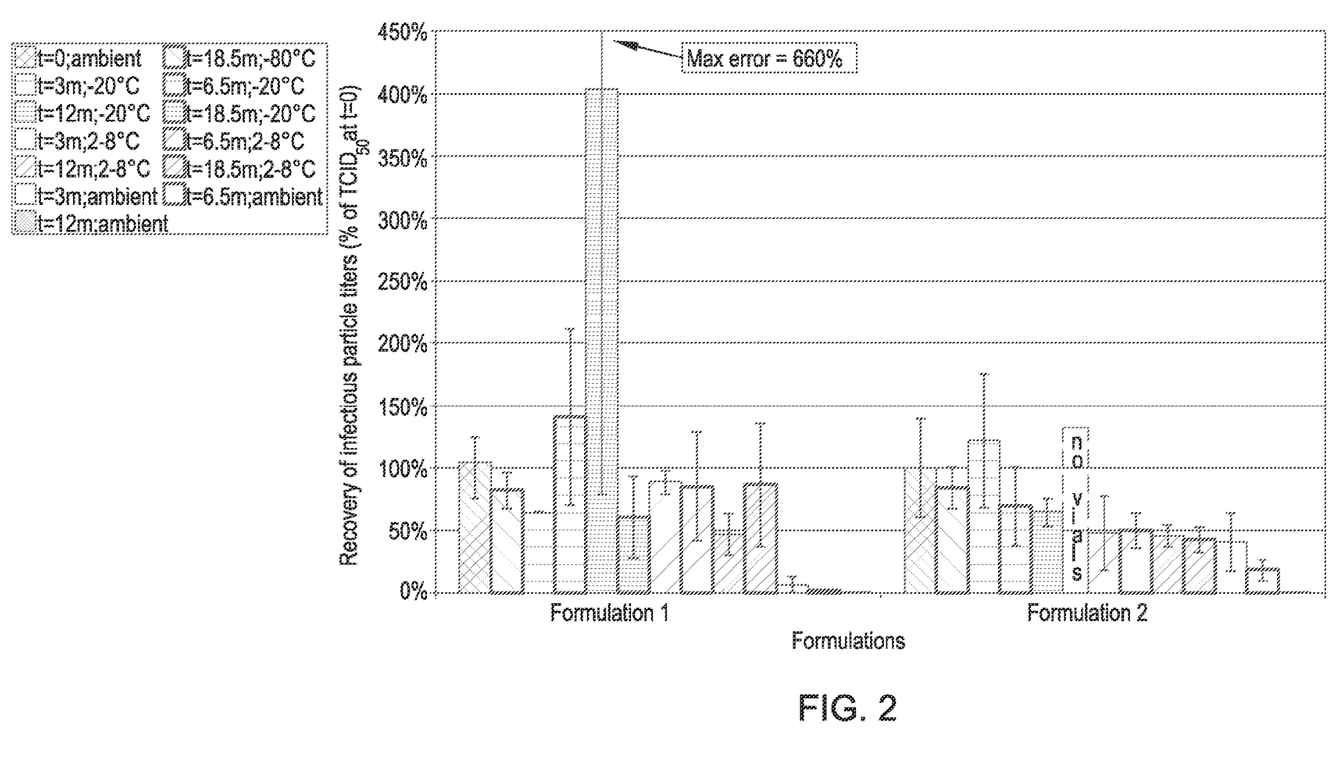
FIG. 2 is a bar graph showing the recovery of infectious particles based on the percentage of median tissue culture infective dose, expressed as $TCID_{50}$ per milliliter, for lyophilized reovirus formulations prior to storage (t=0) at ambient temperature and after 3 (t=3 m), 6.5 (t=6.5 m), 12 (t=12 m), and 18.5 (t=18.5 m) months of storage at ambient temperature, 2-8° C., −20° C., and −80° C. For each formulation, from left to right: t=0 at ambient temperature; t=18.5 m at −80° C.; t=3 m at −20° C.; t=6.5 m at −20° C.; t=12 m at −20° C.; t=18.5 m at −20° C.; t=3 m at 2-8° C.; t=6.5 m at 2-8° C.; t=12 m at 2-8° C.; t=18.5 m at 2-8° C.; t=3 m at ambient temperature; t=6.5 m at ambient temperature; t=12 m at ambient temperature.
Figure 3:
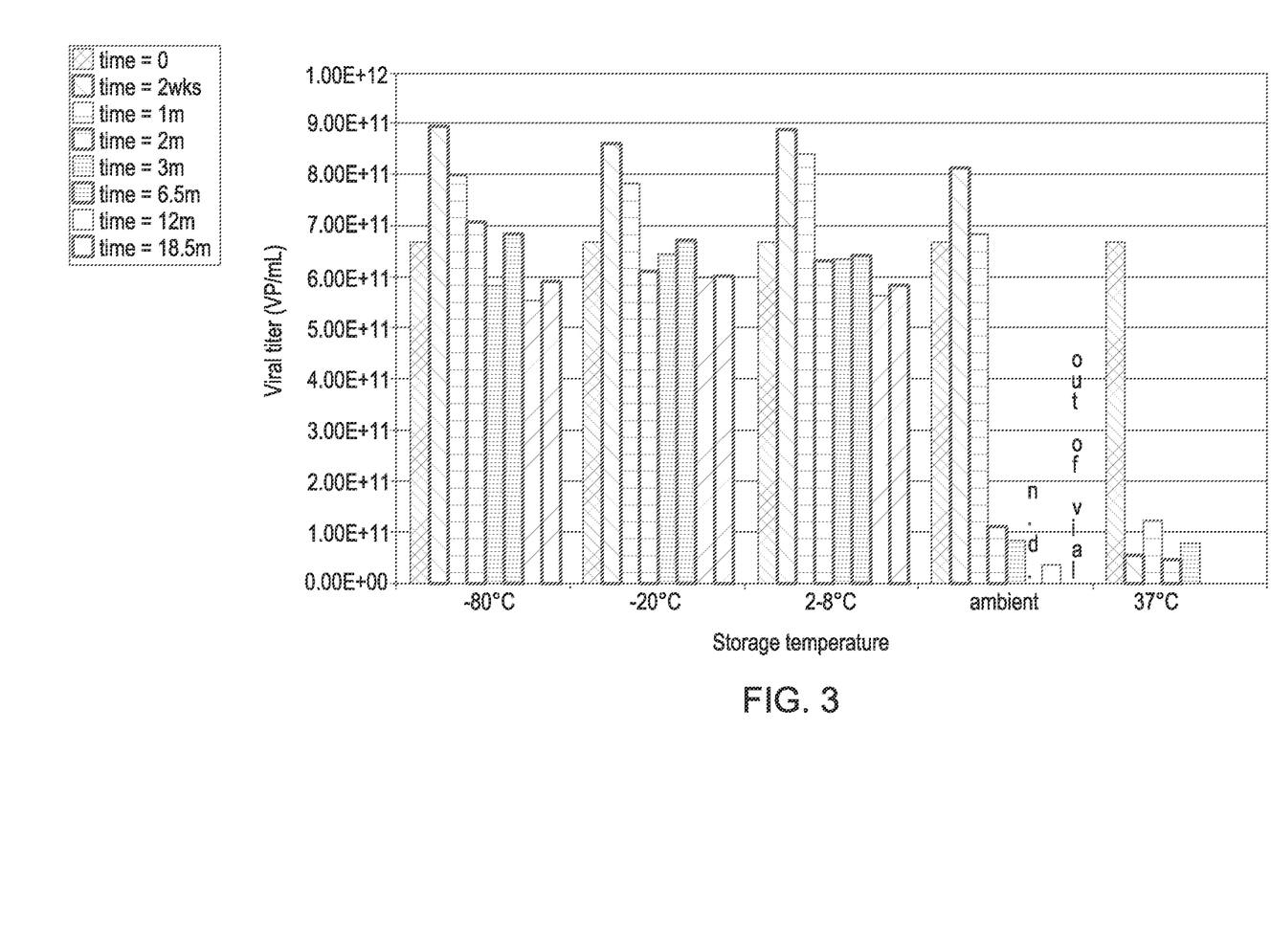
FIG. 3 is a bar graph showing the evolution of the normalized total viral titers measured by HPLC, expressed as viral particles per milliliter, for lyophilized reovirus Formulation 1 prior to storage (t=0) at ambient temperature and after 2 weeks (time=2 wks), 1 month (time=1 m), 2 months (time=2 m), 3 months (time=3 m), 6.5 months (time=6.5 m), 12 months (time=12 m), and 18.5 months (time=18.5 m) of storage at 37° C., ambient temperature, 2-8° C., −20° C., and −80° C. For each temperature, from left to right: time=0, time=2 wks, time=1 m, time=2 m, time=3 m, time=6.5 m, time=12 m, and time=18.5 m.
Figure 4:
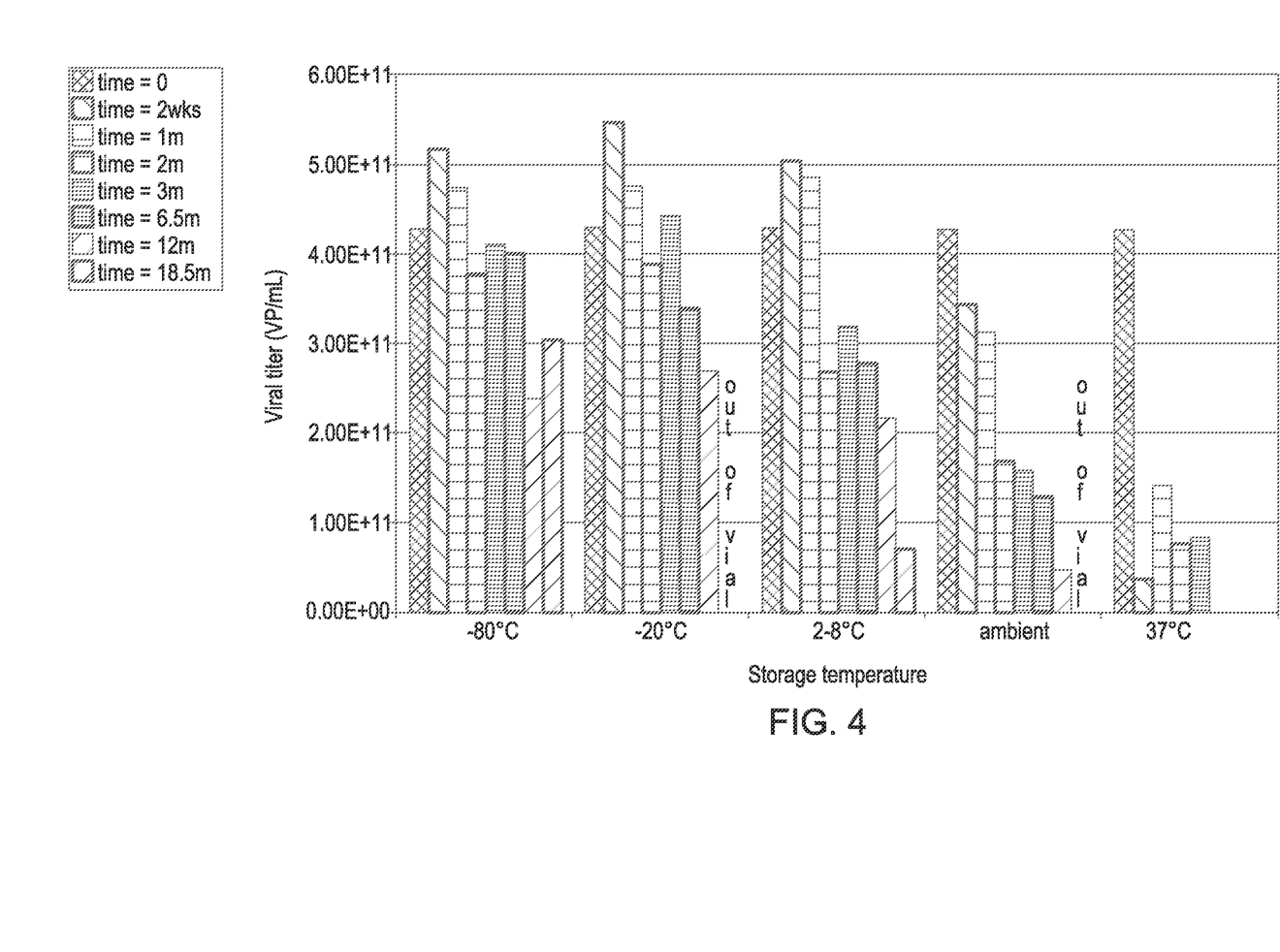
FIG. 4 is a bar graph showing the evolution of the normalized total viral titers measured by HPLC, expressed as viral particles per milliliter, for lyophilized reovirus Formulation 2 prior to storage (t=0) at ambient temperature and after 2 weeks (time=2 wks), 1 month (time=1 m), 2 months (time=2 m), 3 months (time=3 m), 6.5 months (time=6.5 m), 12 months (time=12 m), and 18.5 months (time=18.5 m) of storage at 37° C., ambient temperature, 2-8° C., −20° C., and −80° C. For each temperature, from left to right: time=0, time=2 wks, time=1 m, time=2 m, time=3 m, time=6.5 m, time=12 m, and time=18.5 m. The sample stored for 3 months at −20° C., indicated with an asterisk (*), is from a repeat analysis performed three days after the other storage temperature samples.

The infectious particle titers (TCID$_{50}$/mL) for Control Formulation, Formulation 1, and Formulation 2, as prepared in Example 2, were determined at ambient temperature after preparation (i.e., at time=0). At t=0, the Control Formulation was below the limit of detection, demonstrating that no viable virus was present. Thus, the Control Formulation was not tested at any further timepoints. Formulations 1 and 2 were stored for 0, 3, 6.5, 12 and 18.5 months at different temperatures, including 37° C., ambient temperature, temperatures ranging from 2° C. to 8° C., −20° C., and −80° C. After the storage periods, the $TCID_{50}$ data for each of the formulations at the different temperatures were determined in triplicate. The mean data for Formulations 1 and 2 are shown in FIG. 1. The recoveries of infectious particle titers for Formulations 1 and 2 are shown in FIG. 2. The viral titers were normalized to account for interassay variations in the control titers. The normalized total viral titers, measured by HPLC, are shown in FIG. 3 for Formulation 1 and in FIG. 4 for Formulation 2.

The infectious particle titers of Formulation 1 stored for 3, 6.5, 12, and 18.5 months at −80° C., −20° C., and 2-8° C. were not significantly different from the initial titers obtained at time=0 at ambient temperature. However, in Formulation 1, drops in titer were observed at ambient temperature after 3, 6.5, and 12 months. The infectious particle titers of Formulation 2 stored for 3, 6.5, 12, and 18.5 months at −80° C., −20° C., and 2-8° C. were stable or showed slight decreases in infectivity as compared to the time=0 data. Similarly, slight decreases in infectivity were observed in comparison with the time=0 data after storage for 3 and 6.5 months at ambient temperature. Formulation 2 showed a decrease in infectivity after 12 months.

Example 4

Non-Aggregating Viral Formulations

Samples of Control Formulation and Composition 1, as described above, were tested, prior to lyophilization, for particulate matter using the USP <788> Light Obscuration Particle Count Test. The results, as shown in Table 2, indicate that viral formulations prepared with Composition 1 had many fewer particles than viral formulations using the Control Formulation.

TABLE 2

| # | Final Fill Lot # | Bulk Lot # | Formulation | Mean Particle Diameter (nm) | Particulate matter ≥10 micron #/container | Particulate matter ≥25 micron #/container |
|---|---|---|---|---|---|---|
| 1 | 122-08002 | 160-08001 | Control | 122.3 | 2349 | 32 |
| 2 | 122-08003 | 160-08001 | Control | 114.3 | 2490 | 53 |
| 3 | 160-10006 | 160-10004 | Comp. 1 | 121.8 | 50 | 4 |
| 4 | 160-10011 | 160-10008 | Comp. 1 | 124.9 | 20 | 1 |

What is claimed is:

1. A viral formulation comprising:
(a) a purified virus; and
(b) a non-viral composition comprising:
(i) mannitol;
(ii) sorbitol;
(iii) histidine; and
(iv) $Mg^{2+}$;
wherein the viral formulation is lyophilized;
wherein the non-viral composition, prior to lyophilization, is a liquid non-viral composition further comprising a liquid carrier;
wherein the concentration of sorbitol in the liquid non-viral composition is less than 2.5% based on the weight of the liquid non-viral composition;
wherein the liquid non-viral composition, excluding the liquid carrier, is free of monovalent cationic salts; and
wherein the non-viral composition is provided in an amount effective to stabilize the purified virus.

2. The formulation of claim 1, wherein the combined concentration of mannitol and sorbitol is less than 10% by weight based on the weight of the liquid non-viral composition.

3. The formulation of claim 1, wherein the non-viral composition further comprises a non-ionic surfactant.

4. The formulation of claim 3, wherein the non-ionic surfactant is polysorbate 80.

5. The formulation of claim 1, wherein the viral formulation is substantially free of trehalose or free of $Zn^{2+}$.

6. The formulation of claim 1, wherein the virus is an oncolytic virus, a non-enveloped virus, or a reovirus.

7. The formulation of claim 1, wherein $Mg^{2+}$ is present as magnesium chloride.

8. The formulation of claim 1, wherein the liquid carrier is an aqueous carrier.

9. The formulation of claim 1, wherein the viral formulation is stable at a temperature at about ambient temperature.

10. The formulation of claim 1, wherein the viral formulation is stable at a temperature of about 4° C. or lower for at least three months, at least six months, at least twelve months, or at least eighteen months.

11. The formulation of claim 1, which is suitable for reconstitution before administration.

12. A method of making a viral formulation, comprising the steps of:
(a) providing a virus;
(b) combining, to form a liquid viral formulation, the virus and a liquid non-viral composition, wherein the liquid non-viral composition comprises:
(i) mannitol;
(ii) sorbitol in a concentration of less than 2.5% based on the weight of the non-viral composition;
(iii) histidine;
(iv) $Mg^{2+}$; and
(v) a liquid carrier, and
wherein the non-viral composition, excluding the liquid carrier, is free of monovalent cationic salts; wherein the non-viral composition is provided in an amount effective to stabilize the purified virus; and
(c) lyophilizing the liquid viral formulation,
to form a viral formulation.

13. The method of claim 12, wherein the combined concentration of mannitol and sorbitol in the non-viral composition is less than 10% by weight based on the weight of the non-viral composition.

14. The method of claim 12, further comprising adding a non-ionic surfactant to the liquid non-viral composition.

15. The method of claim 14, wherein the non-ionic surfactant is polysorbate 80.

16. The method of claim 12, wherein the viral formulation is substantially free of trehalose or free of $Zn^{2+}$.

17. The method of claim 12, wherein lyophilizing the liquid viral formulation comprises:
(a) freezing the liquid viral formulation to a temperature lower than 0° C. to form a frozen viral formulation; and
(b) applying a vacuum to the frozen viral formulation.

18. The method of claim 12, further comprising reconstituting the lyophilized viral formulation.

19. The method of claim 18, wherein reconstituting the lyophilized viral formulation comprises dissolving or suspending the lyophilized viral formulation in a medium.

20. The method of claim 12, wherein the virus is an oncolytic virus, a non-enveloped virus, or a reovirus.

21. The method of claim 12, wherein $Mg^{2+}$ is present as magnesium chloride.

22. The method of claim 12, wherein the liquid carrier is an aqueous carrier.

23. A viral formulation prepared according to the method of claim 12.

24. A method of preserving or stabilizing a virus, comprising:
   preparing a viral formulation according to claim 1; and
   storing the viral formulation.

25. The method of claim 24, wherein the virus is stored at a temperature at or below ambient temperature.

26. The method of claim 24, wherein the temperature is selected from the group consisting of ambient temperature, from 2° C. to 8° C., 4° C., −20° C., and from −60° C. to −80° C.

27. A method of preparing a non-aggregating viral formulation, comprising preparing a viral formulation according to claim 1.

28. The method of claim 27, wherein the formulation is suitable for administration by parenteral infusion or injection.

29. The formulation of claim 6, wherein the reovirus is selected from the group consisting of a mammalian reovirus, a recombinant or reassorted reovirus, and IDAC #190907-01.

30. The formulation of claim 29, wherein the mammalian reovirus is a human reovirus.

31. The formulation of claim 30, wherein the human reovirus is a serotype 3 reovirus.

32. The formulation of claim 31, wherein the serotype 3 reovirus is a Dearing strain serotype 3 reovirus.

33. The method of claim 20, wherein the reovirus is selected from the group consisting of a mammalian reovirus, a recombinant or reassorted reovirus, and IDAC #190907-01.

34. The method of claim 33, wherein the mammalian reovirus is a human reovirus.

35. The method of claim 34, wherein the human reovirus is a serotype 3 reovirus.

36. The method of claim 35, wherein the serotype 3 reovirus is a Dearing strain serotype 3 reovirus.

37. A non-viral composition for use in preserving or stabilizing a virus comprising:
   (a) mannitol;
   (b) sorbitol;
   (c) histidine; and
   (d) $Mg^{2+}$;
   (e) a liquid carrier,
   wherein the formulation is lyophilized;
   wherein the non-viral composition, prior to lyophilization, is a liquid non-viral composition further comprising a liquid carrier,
   wherein the concentration of sorbitol in the liquid non-viral composition is less than 2.5% based on the weight of the liquid non-viral composition;
   wherein the non-viral composition, excluding the liquid carrier, is free of monovalent cationic salts; and wherein the non-viral composition is provided in an amount effective to stabilize said virus.

* * * * *